United States Patent
Hoernig

(10) Patent No.: US 9,629,594 B2
(45) Date of Patent: Apr. 25, 2017

(54) CONTRAST-ENHANCED IMAGING OF OBJECTS

(71) Applicant: SIEMENS AKTIENGESELLSCHAFT, Munich (DE)

(72) Inventor: Mathias Hoernig, Erlangen (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 549 days.

(21) Appl. No.: 14/022,720

(22) Filed: Sep. 10, 2013

(65) Prior Publication Data
US 2014/0072096 A1 Mar. 13, 2014

(30) Foreign Application Priority Data
Sep. 10, 2012 (DE) .......................... 10 2012 215 997

(51) Int. Cl.
*A61B 6/00* (2006.01)
*A61B 6/02* (2006.01)

(52) U.S. Cl.
CPC .............. *A61B 6/481* (2013.01); *A61B 6/025* (2013.01); *A61B 6/482* (2013.01); *A61B 6/502* (2013.01); *A61B 6/4035* (2013.01)

(58) Field of Classification Search
CPC ......... A61B 6/025; A61B 6/502; A61B 6/481; A61B 6/482
See application file for complete search history.

(56) References Cited

U.S. PATENT DOCUMENTS 7,684,598 B2   3/2010  Hidebrand et al.
2004/0101089 A1  5/2004  Karau et al.
(Continued)

FOREIGN PATENT DOCUMENTS

DE   102004034503 A1   2/2006
DE   102011003135 A1   7/2012

OTHER PUBLICATIONS

Carton et al. Dual-energy contrast-enhanced digital breast tomosynthesis—a feasibility study. Apr. 2010. The British Journal of Radiology, 83 (2010) 344-350.*

(Continued)

*Primary Examiner* — Dani Fox
(74) *Attorney, Agent, or Firm* — Laurence Greenberg; Werner Stemer; Ralph Locher

(57) ABSTRACT

A contrast-enhanced imaging of an object is performed by an imaging device having a movable radiation source. A first projection image sequence of the object along a first trajectory over which the radiation source moves is recorded by radiation having a first energy spectrum. Subsequently, a second projection image sequence of the object along a second trajectory over which the radiation source moves is recorded by radiation having a second energy spectrum. A reconstruction of a three-dimensional subtraction image in relation to the different energy spectra is carried out by the first and second projection image sequence. In addition, a two-dimensional subtraction image in relation to the different energy spectra is reconstructed with the aid of the first and second projection image sequence. In this way, apart from a three-dimensional subtraction image, a two-dimensional subtraction image is also provided for better analysis of object characteristics.

10 Claims, 3 Drawing Sheets

(56) References Cited

U.S. PATENT DOCUMENTS

| | | |
|---|---|---|
| 2009/0123052 A1 | 5/2009 | Ruth et al. |
| 2010/0135558 A1 | 6/2010 | Ruth et al. |
| 2010/0166267 A1 | 7/2010 | Zhang et al. |
| 2012/0189091 A1 | 7/2012 | Jerebko |
| 2012/0238870 A1* | 9/2012 | Smith .................. A61B 6/025 600/431 |

OTHER PUBLICATIONS

M. Hoernig, et al. "Design of a contrast enhanced dual energy tomosynthesis system for breast cancer imaging", Medical Imaging 2012: Physics of Medical Imaging. Proceedings of the SPIE, vol. 8313, pp. 831340-831340-9 (2012); 2012.

* cited by examiner

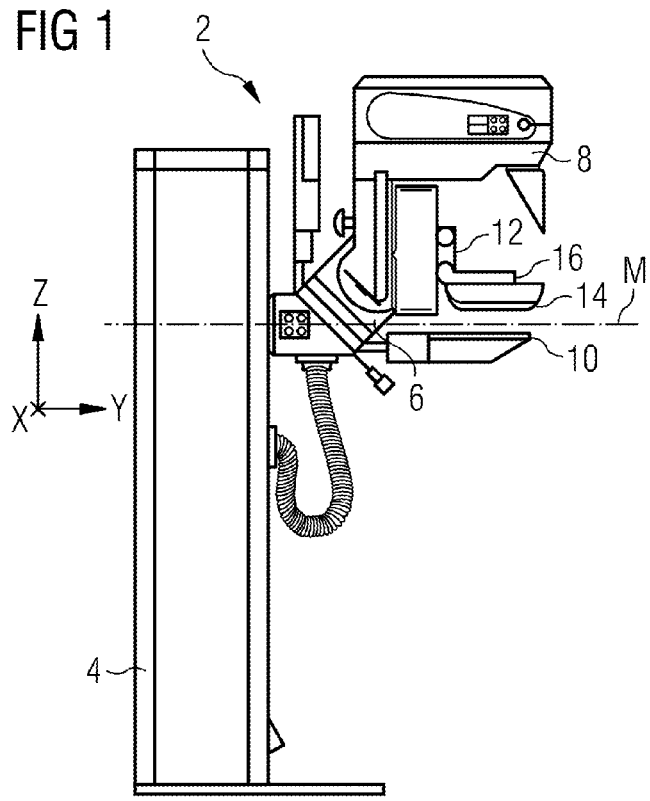
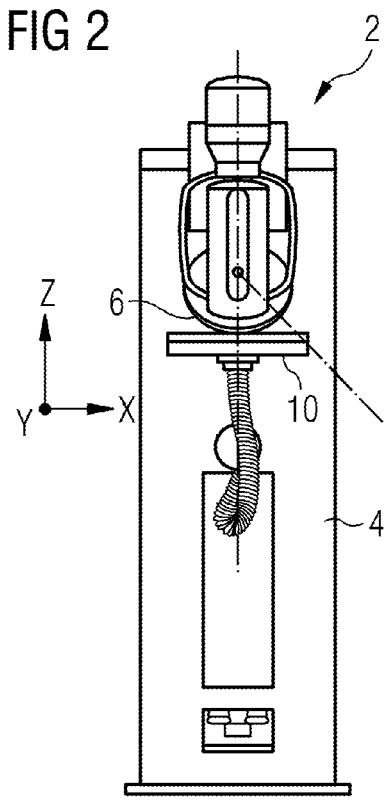
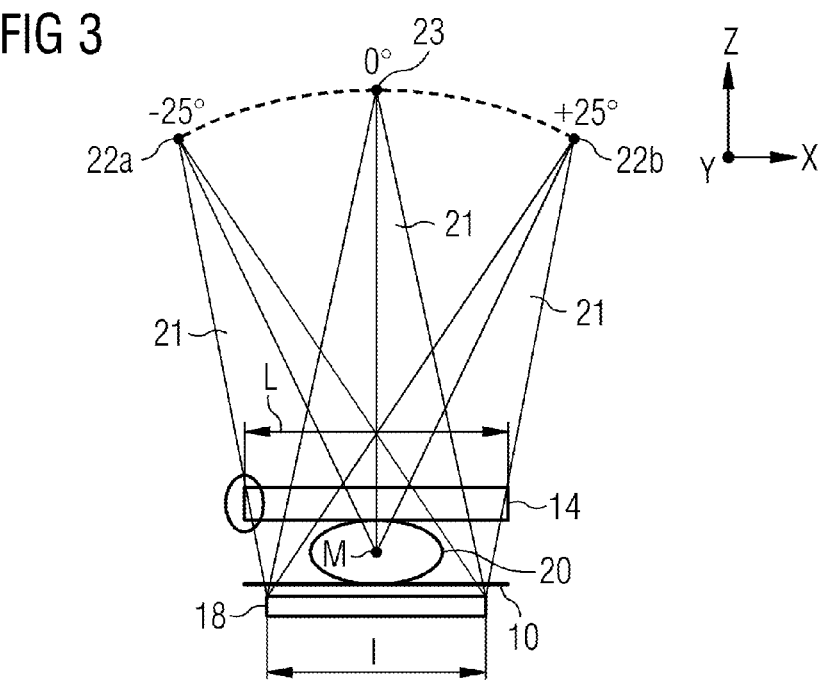

CONTRAST-ENHANCED IMAGING OF OBJECTS

CROSS-REFERENCE TO RELATED APPLICATION

This application claims the priority, under 35 U.S.C. §119, of German application DE 10 2012 215 997.5, filed Sep. 10, 2012; the prior application is herewith incorporated by reference in its entirety.

BACKGROUND OF THE INVENTION

Field of the Invention

The invention relates to a method and a device for contrast-enhanced imaging of an object.

X-ray devices are widely used in medical diagnostics. Some X-ray diagnostic devices are specifically configured for particular examinations in order to take account of the particular requirements of such examinations. An example of a special diagnostic device is a mammography device for examining the breast tissue of female patients. In order to improve the imaging quality, the breast to be examined is compressed with the aid of a compression plate. In the context of a mammography examination, X-rays are emitted by an X-ray source, penetrate the compressed breast and are then detected by a detector.

Conventional examinations using mammography typically involve a single image recording or two image recordings from different angles (mediolateral oblique (MLO) and craniocaudal (CC) recordings). In a recording of this type, the attenuation of the X-rays while passing through the tissue is detected. The attenuation is dependent on the density of the tissue through which the radiation passes. Due to the changed density of diseased tissue, from the recording or recordings, diseased tissue can be diagnosed. An important limitation of this procedure lies in the fact that information concerning a three-dimensional object (breast tissue) is collected by a detector with a resolution in two dimensions. In the direction of the X-ray beam (i.e. perpendicular to the detector surface) it is only overall information (total attenuation) that is obtained, which means that there is practically no resolution. This limitation can lead to false diagnoses.

A further development of conventional mammography which permits resolution orthogonally to the detector surface is tomosynthesis. In the course of tomosynthesis, the X-ray source passes along a trajectory (typically an arc of e.g.) 50°. During the movement along the trajectory, recordings are made from different angles (e.g. 10-50 recordings). From this plurality of recordings, a three-dimensional image of the object being examined can be obtained or reconstructed by reconstruction algorithms. The three-dimensional image enables better diagnosis and localization of diseased tissue.

Even when tomosynthesis is used, due to the small difference between the attenuation coefficients of healthy and diseased tissue, some carcinomas remain undiscovered. An improvement comes from the use of contrast medium (e.g. iodine) in the context of digital contrast medium mammography ("contrast enhanced digital mammography", CEDM) with the result that lesions can be discovered better due to the neovascularization in tumors.

Digital contrast medium mammography ("contrast enhanced digital mammography", CEDM) is a technology existing in different versions in which—as distinct from conventional mammography—image data can be recorded from a positionally fixed, typically compressed, breast from different angles and then later can be reconstructed in high resolution in a set of thin slice image recordings. When compared with conventional X-ray mammography, tomosynthesis has a large number of advantages. In particular, pathological structures can be recognized more easily because interference signals from overlaid tissue portions and artifacts are reduced.

In principle, there are two fundamental possibilities for performing a contrast medium mammography.

First, there is digital dynamic subtraction mammography, a first pre-contrast recording of the breast being compared with a second contrast medium-enhanced reference recording.

Second, is dual-energy subtraction mammography (CE-DEM: contrast enhanced dual energy mammography) in which, following application of a typically iodine-containing contrast medium, two recordings are made at different energy levels. Due to the resulting different absorption properties, following logarithmic subtraction of the two recordings, the contrast medium enhancement can be imaged.

Dual-energy subtraction mammography can be extended to a dual-energy subtraction tomosynthesis wherein, following injection of a contrast medium, two tomoscans are performed at different energies. Such tomosynthesis methods with two energy levels are also referred to as contrast enhanced dual energy tomosynthesis (CEDET) methods. The procedure with these methods is described in greater detail, for example, in the scientific publication "Design of a Contrast-Enhanced Dual-Energy Tomosynthesis System for Breast Cancer Imaging" by M. D. Hörnig, L. Bätz and T. Mertelmeier in Medical Imaging 2012: Physics of Medical Imaging, edited by Pelc, Norbert J.; Nishikawa, Robert M.; Whiting, Bruce R. Proceedings of the SPIE, volume 8313, pp. 831340-831340-9 (2012).

Even if the CEDET method represents a significant improvement over conventional mammography, there is a need to provide the diagnosing physician with as much information of relevance to the diagnosis as possible.

SUMMARY OF THE INVENTION

It is an object of the invention to improve dual-energy imaging in this regard.

With the foregoing and other objects in view there is provided, in accordance with the invention a method for contrast-enhanced imaging of an object by an imaging device having a movable radiation source. The method includes the steps of: recording a first projection image sequence of the object along a first trajectory over which the movable radiation source moves, by means of radiation having a first energy spectrum; and recording a second projection image sequence of the object along a second trajectory over which the movable radiation source moves, by means of the radiation having a second energy spectrum, the first and second energy spectra being different energy spectra. A three-dimensional subtraction image is reconstructed in relation to the different energy spectra by the first and second projection image sequences. At least one two-dimensional subtraction image is reconstructed in relation to the different energy spectra with an aid of the first and second projection image sequences. The three-dimensional subtraction image together with the at least one two-dimensional subtraction image are provided for an analysis of object characteristics.

According to the invention, an object, for example, a patient is subjected to a contrast-enhanced recording technique. Use is made herein of a movable radiation source, for example, an X-ray source (mammography device, C-arm, computed tomograph, etc.) as part of an imaging device. According to the invention, a first projection image sequence or projection image chain of the object is recorded along a first trajectory over which the radiation source moves. The radiation used by the first recording of a sequence has a first energy spectrum with, typically, low energies. This energy spectrum preferably consists, as far as possible, of monochrome radiation energy. The energy spectrum is changed for a second recording of a projection image sequence. This is achieved, for example, by using suitable radiation filters or by suitable control of the radiation source (e.g. operating the radiation source at two different voltage levels). The second projection image sequence of the object is created with radiation having a second energy spectrum (typically of high radiation energy) along a second trajectory. The energy spectra used for the image sequence recordings differ, so that with these recordings, different projections are recorded, even if identical trajectories are used. The first and second trajectories can overlap partially or completely—it is also conceivable for the first and second trajectory to adjoin one another so that positional adjustment of the recording system before the start of the second trajectory is not necessary.

Using the two projection image sequences, a three-dimensional subtraction image is reconstructed. In addition, at least one two-dimensional subtraction image is generated or constructed for projections recorded with different energy spectra with the aid of the first and second projection image sequences. In the reconstruction of the two-dimensional subtraction image, an angle-dependent weighting can be carried out. A plurality of two-dimensional subtraction images can also be constructed from different directions, for example, when tomosynthesis is used, a CC recording and an MLO recording.

The two-dimensional subtraction image can be obtained by forward projection of the three-dimensional subtraction image, or directly from a difference between projection images of the first and second projection image sequences. Construction using forward projection suggests itself in particular if, for the desired angle, no projection images from the two projection image sequences are present for the desired angle, which can be the case if the trajectories do not match.

For the construction of the two-dimensional subtraction image, a weighting and/or filtration of projections recorded at high energy can be carried out.

According to the invention, the three-dimensional subtraction image is made available together with the two-dimensional subtraction image for analysis or diagnosis. This can be achieved, for example, in that both the three-dimensional and the two-dimensional information is available at a workstation and can be observed, for example, by a display. It is herein conceivable that both two-dimensional and three-dimensional representations are displayed simultaneously or alternately by the display.

The invention permits—in particular with dual-energy applications in conjunction with a previous administration of contrast medium—the user of the information (the diagnosing physician or the personnel investigating the object) to be offered a more complete representation of the object which contains two-dimensional and three-dimensional information. In this way, particularly in medical uses requiring the greatest care, for example, in cancer diagnosis, false diagnoses are made less likely.

The invention also includes a device for contrast-enhanced recording of an object which contains an imaging device made of a pair consisting of a radiation source and a radiation detector assigned to one another. This source-detector pair is movable along trajectories around the object (e.g. circular trajectory, spiral trajectory, etc.), such that the recording of projection image sequences of the object along trajectories followed by the radiation source using radiation having an adjustable energy spectrum is made possible. The device also has a first computer unit for reconstructing a three-dimensional subtraction image in relation to different energy spectra using different projection image sequences. In addition, a second computer unit is provided (which can be identical to the first). The computer unit is used for constructing two-dimensional subtraction images in relation to different energy spectra with the aid of different projection image sequences. The two computer units can be physical units or can be realized with software. Implementation partly by hardware and partly by software is also conceivable. The device also contains a display unit in order to provide a three-dimensional subtraction image together with a two-dimensional subtraction image for analysis or diagnosis of object properties.

Other features which are considered as characteristic for the invention are set forth in the appended claims.

Although the invention is illustrated and described herein as embodied in contrast-enhanced imaging of objects, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a diagrammatic, side view of a mammography device according to the invention;

FIG. 2 is a front view of the mammography device of FIG. 1;

FIG. 3 is an illustration of two deflection positions on irradiation by the mammography device for a tomosynthesis procedure;

DETAILED DESCRIPTION OF THE INVENTION

Figure 4:
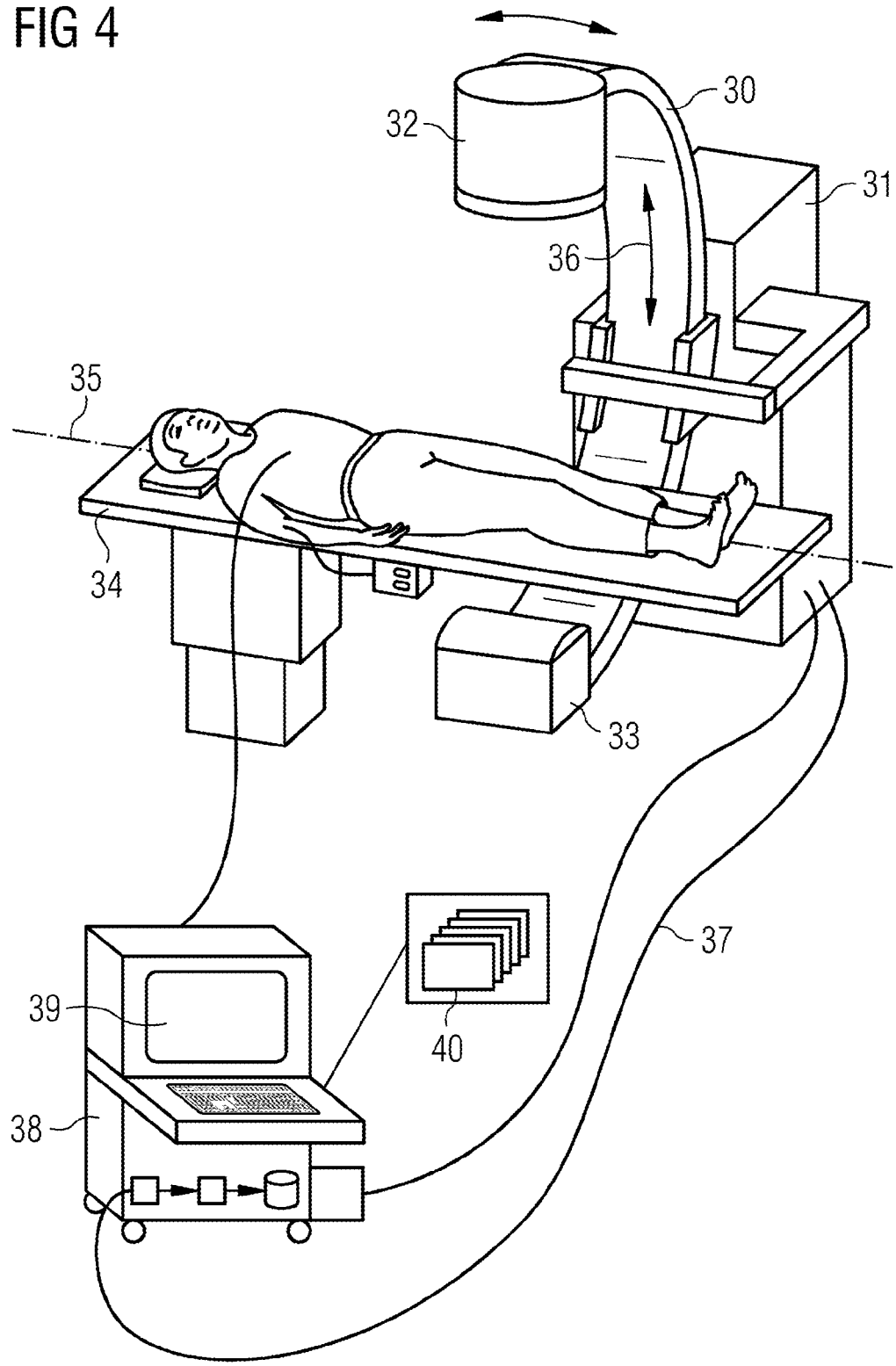
FIG. 4 is a diagrammatic, perspective view of a C-arm system suitable for carrying out the invention.

Referring now to the figures of the drawing in detail and first, particularly, to FIGS. 1 and 2, there is shown a side view and a front view of a mammography device 2. The mammography device 2 has a base element configured as a stand 4 and a device arm 6 projecting from the stand 4, having an irradiating unit 8 configured as an X-ray radiator arranged at a free end of the device arm. Also arranged on the device arm 6 are an object table 10 and a compression unit 12. The compression unit 12 contains a compression element 14 which is arranged displaceable relative to the object table 10 along a vertical Z-direction, and a holder 16 for the compression element 14. A type of lift guideway is provided in the compression unit 12 for displacing the holder 16 together with the compression element 14. Also, arranged in a lower region of the object table 10 is a detector 18 (see FIG. 3) which in this exemplary embodiment is a digital detector.

The mammography device 2 is provided, in particular, for tomosynthesis examinations, the radiation unit 8 being moved through an angular region about a central axis M extending parallel to the Y-direction, as shown in FIG. 3. In this process, a plurality of projections of an object 20 to be examined, which is held positionally fixed between the object table 10 and the compression element 14 is obtained. During the image recordings from the widely varying angular positions, an X-ray beam 21 of conical or fan-like shape in cross-section penetrates the compression element 14, the object 20 under examination and the object table 10 and impinges upon the detector 18. The detector 18 is dimensioned such that the image recordings can be made in an angular range between two deflection positions 22a, 22b at corresponding deflection angles of −25° and +25°, respectively. The deflection positions 22a, 22b are arranged in the X-Z plane on either side of a zero position 23 in which the X-ray beam 21 impinges vertically on the detector 18. In this exemplary embodiment, in particular, the flat detector 18 has a size of 24 cm×30 cm.

On passing along the path from the point 22a to the point 22b, for example, 25 recordings are made. From the projections recorded, an image is determined iteratively for the object 20 under examination.

In addition to a mammography device of this type suitable for CEDET methods, other medical arrangements can also be used for dual-energy image formation.

The invention can, for example, also be realized with another X-ray system such as the C-arm shown in FIG. 4. Here, a C-arm 30 is shown fastened to a stand 31. The C-arm has a source 32 and a detector 33. As indicated by the arrow 36, the C-arm 30 is rotatable about an axis 35, such that recordings of a patient lying on a support 34 can be made from various directions. In this way, a projection image sequence can also be generated with the C-arm 30. The projections obtained in this way are transmitted by a connection 37 to a control center and/or workstation 38 which has programs 40 for processing the projections. The workstation also has a display or a monitor 39 with which the two or three-dimensional images can be viewed.

When the arrangements shown in FIGS. 1 and 4 are used for the contrast-enhanced dual-energy examination, typically after prior contrast medium injection, a low-energy scan is carried out followed by a high-energy scan. The recorded images are registered or identified such that identification of the images of both scans relative to one another is possible. This is also useful because, due to the recording conditions (patient movement, compression situation, etc.), unambiguous allocation is not always possible by visual comparison alone.

In the case of a tomosynthesis examination, the breast compression is maintained for both scans. A reconstruction of two images, respectively from one of the two image sequences (from the whole sequence or from a part of the projections contained in the sequence), is then carried out and a weighted subtraction of the reconstructed images, so that essentially a representation of the contrast medium enrichment is obtained. The representation or the resulting subtraction image is largely characterized in that the parenchyma is suppressed in the image and only the contrast medium is depicted.

According to the invention, both two-dimensional and three-dimensional dual-energy results are prepared in parallel. In the case of a tomosynthesis examination, this would provide a combination of CEDET and CEDEM methods. This will now be described in greater detail by reference to FIG. 5. In step K, which is not obligatory for every imaginable dual-energy examination, first, a contrast medium is injected. In a second step, a first trajectory is followed, resulting in a first projection image sequence S1. For the preparation of a second projection image sequence S2 or for a second tomoscan, in step E, the energy of the radiation is increased, for example, by using a different filter for the radiation or by increasing the voltage of the X-ray source. At the higher energy, a second trajectory is then followed, resulting in the second projection image sequence S2. From these two projection image sequences, a three-dimensional subtraction image 3DB and a two-dimensional subtraction image 2DB are then generated. A first method for generating the three-dimensional subtraction image 3DB is indicated with continuous arrows. From the results of the scans S1 and S2, an image is then reconstructed in the reconstruction steps R1 and R2. In the image space, the difference is then calculated in a step D14, so that the three-dimensional subtraction image 3DB is produced.

A second possibility is indicated by dashed lines. The projection image sequences S1 and S2 obtained by the trajectories are directly subtracted from one another (step D14) and then reconstructed into a three-dimensional subtraction image 3DB (step RD14). The image reconstruction is carried out with conventional methods here, for example, a Feldkamp algorithm or a filtered back projection (FBP) method. Both iteratively and mathematically precise reconstruction methods can be used. A first procedure for generating a two-dimensional subtraction image 2DB is indicated by dashed arrows. Here, the projection image sequences S1 and S2 are directly subtracted from one another (step D14), resulting in the two-dimensional subtraction image 2DB. The subtraction D14 can undergo weighting by which non-relevant structures are better suppressed. During the weighting, for example, the formula $\ln(I_{REC})=-\mu*\ln(I_{LE})+\ln(I_{HE})$ is used, where $I_{REC}$ represents the result constructed from the recording $I_{LE}$ at lower energy and the recording $I_{HE}$ at higher energy. In the recombined image, only the contrast medium is shown and the parameter $\mu$ is selected for subtractive removal of the background (typical values for $\mu$ are 0.15 . . . 0.3).

Figure 5:
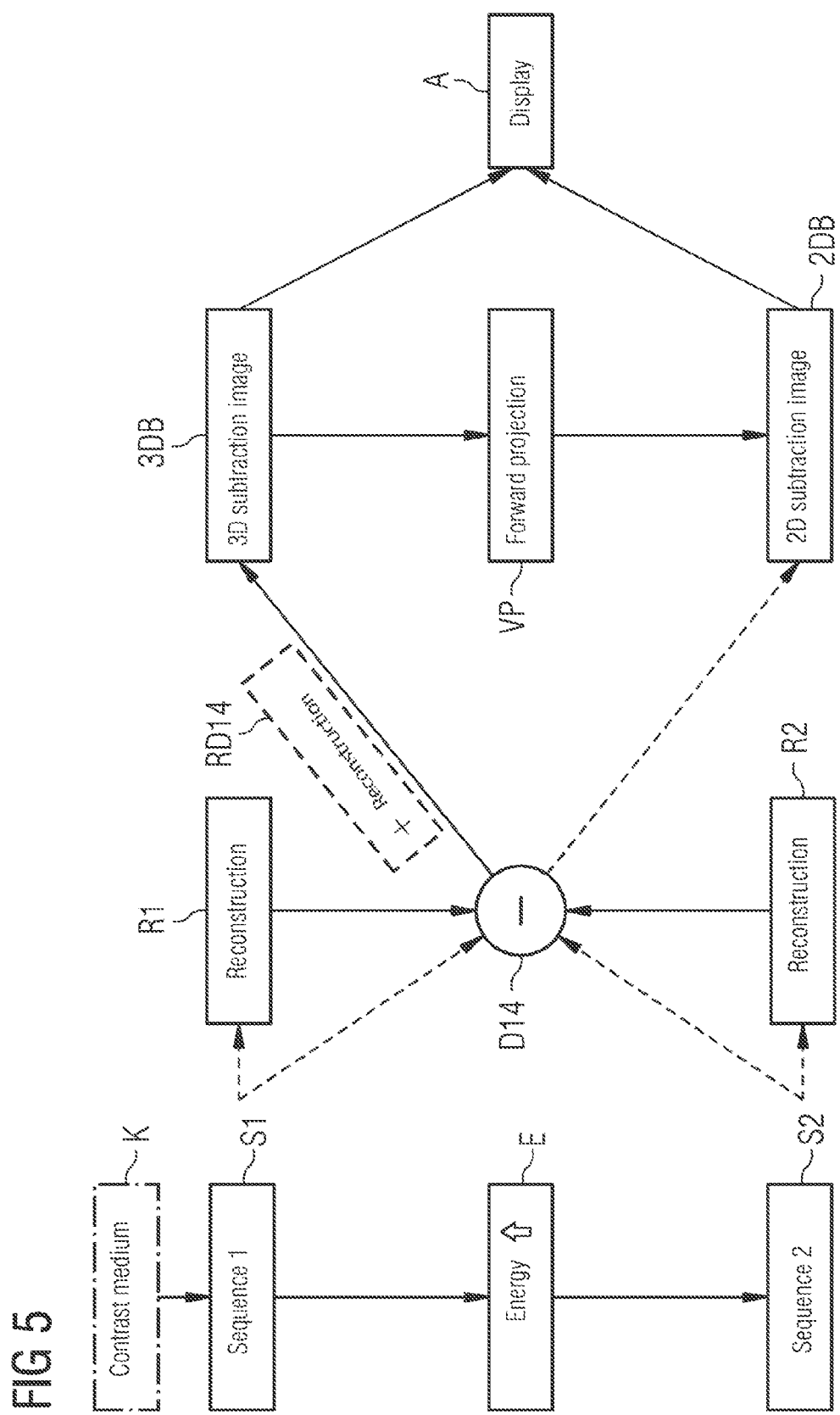
FIG. 5 is a diagram illustrating the method according to the invention.

It is possible that the projection recordings S1 and S2 were not made for the same angular positions. For example, for the tomosynthesis, it is conceivable that the projections of the first scan are uneven (1°, 3°, 5° . . . ) and those of the second scan are even (0°, 2°, 4° . . . ). Although a direct calculation of the two-dimensional subtraction image might be possible through interpolation of projection images, another method is preferably used here. This is shown in FIG. 5 with the solid arrows. In this case, a two-dimensional subtraction image 2DB is generated from the three-dimensional subtraction image 3DB by forward projection VP. In the calculation of the two-dimensional subtraction image 2DB, which is a resultant CEDEM image for the tomosynthesis, the projection images are preferably differently weighted as a function of the resulting angle (e.g. 0° C.). Preferably, smaller angles are more strongly weighted. The weighting can be taken into account as early as when a three-dimensional reconstruction image for both energies is created. Subsequently, the calculation of the synthetic CEDEM resultant image from a subset of the reconstructed volume is then carried out.

This type of calculation of CEDEM resultant images also enables, inter alia, depending on the objective, a resultant image to be generated which differs from the standard projections (CC and MLO positions) for a different projection angle (e.g. 10°).

The three-dimensional subtraction image 3DB and the two-dimensional subtraction image 2DB are then together made available to the physician or personnel for the diagnosis with the aid of a display.

This method is not restricted to tomosynthesis. It can also be transferred to other dual-energy uses (temporary subtractions), such as for the stomach, the swallowing process or the lungs. Uses without contrast medium administration are also conceivable.

The invention claimed is:

1. A method for contrast-enhanced imaging of an object by an imaging device having a movable x-ray radiation source, which comprises the steps of:
   recording a first projection image sequence of the object along a first trajectory over which the movable x-ray radiation source moves, with a detector detecting x-ray radiation having a first energy spectrum;
   recording a second projection image sequence of the object along a second trajectory over which the movable x-ray radiation source moves, with the detector detecting x-ray radiation having a second energy spectrum, the first and second energy spectra being different energy spectra;
   reconstructing a three-dimensional subtraction image in relation to the different energy spectra using the first and second projection image sequences;
   reconstructing at least one two-dimensional subtraction image in relation to the different energy spectra by forward projection of the three-dimensional subtraction image; and
   providing the three-dimensional subtraction image together with the at least one two-dimensional subtraction image for an analysis of object characteristics.

2. The method according to claim 1, which further comprises:
   providing an organism as the object; and
   recording one of the first or second projection image sequences after administration of a contrast medium.

3. The method according to claim 1, wherein:
   a shape of the first and second trajectories can be described with an aid of an angle; and
   in the reconstruction of the two-dimensional subtraction image, an angle-dependent weighting is carried out.

4. The method according to claim 1, which further comprises reconstructing a plurality of two-dimensional subtraction images from different directions.

5. The method according to claim 1, which further comprises generating the different energy spectra using different x-ray radiation filters or different x-ray radiation source control parameters.

6. The method according to claim 1, which further comprises carrying out weighting or filtration of image projections recorded with energy spectra containing higher energies.

7. The method according to claim 1, wherein:
   the method is used in a context of a mammographic examination; and
   the at least one two-dimensional subtraction image corresponds to a craniocaudal recording or a mediolateral oblique recording.

8. The method according to claim 1, which further comprises using the method for examining a stomach, lungs or esophagus.

9. A device for contrast-enhanced imaging of an object, the device comprising:
   an imaging device having an x-ray radiation source-radiation detector pair with an x-ray radiation source assigned to a radiation detector, the x-ray radiation source movable along trajectories around the object, said imaging device configured to record projection image sequences of the object along the trajectories over which said x-ray radiation source moves using x-ray radiation having an adjustable energy spectrum;
   a first computer unit for reconstructing a three-dimensional subtraction image in relation to different energy spectra using different projection image sequences;
   a second computer unit for constructing two-dimensional subtraction images in relation to the different energy spectra by forward projection of the three-dimensional subtraction image; and
   a display unit for providing the three-dimensional subtraction image together with the two-dimensional subtraction image for an analysis of object characteristics.

10. The device according to claim 9, wherein the different energy spectra are set using at least one of different x-ray radiation filters or different x-ray radiation source control parameters.

* * * * *